United States Patent [19]

Teller

[11] 4,091,102
[45] May 23, 1978

[54] ANTI-DEPRESSANT TRANS-HEXAHYDROPYRIDO[3,4-B]INDOLES

[75] Inventor: Sonia Ruth Teller, Louisville, Ky.

[73] Assignee: Endo Laboratories, Inc., Garden City, N.Y.

[21] Appl. No.: 695,361

[22] Filed: Jun. 22, 1976

Related U.S. Application Data

[63] Continuation-in-part of Ser. No. 606,871, Aug. 22, 1975, abandoned.

[51] Int. Cl.$^2$ .................. A61K 31/445; C07D 471/04
[52] U.S. Cl. .............................. 424/256; 260/293.55; 260/295 T; 260/29 GT; 260/319.1; 260/326.13 B; 424/267
[58] Field of Search ................... 260/293.55; 424/267, 424/256

[56] References Cited

U.S. PATENT DOCUMENTS

| 2,642,438 | 6/1953 | Duschinsky | 260/296 |
| 3,657,254 | 4/1972 | Barkov et al. | 260/293.55 |

OTHER PUBLICATIONS

Djerassi et al., J. Am. Chem. Soc. 88:8, 1792–1798(1966).
Gribble et al., J. Am. Chem. Soc. 96:25, 7812–7814(1974).
Marshall et al., J. Org. Chem. 28, 421–423(1963).

Primary Examiner—Natalie Trousof

[57] ABSTRACT

Novel trans-hexahydropyrido[3,4-b]indoles and their suitable pharmaceutical salts useful for alleviating depression in mammals.

9 Claims, No Drawings

ANTI-DEPRESSANT TRANS-HEXAHYDROPYRIDO[3,4-B]INDOLES

CROSS-REFERENCE TO RELATED APPLICATION

This is a continuation-in-part of my copending application Ser. No. 606,871, filed Aug. 22, 1975, now abandoned.

BACKGROUND OF THE INVENTION

This invention relates to substituted pyridoindole anti-depressants.

Clin-Midy, in British Pat. No. 1,382,943 and Canas-Rodriquez & Leeming in British Pat. No. 1,220,628 disclose various intermediates used in the preparation of compounds of this invention.

Duschinsky, in U.S. Pat. No. 2,642,438 discloses 9-aryl-2-substituted-1,2,3,4-tetrahydro-9H-pyrido[3,4-b]indoles useful as spasmolytics and adrenolytics, and 1-phenyl-3-(β-aminoethyl)indole and its derivatives which are intermediates in the preparation of compounds of this invention. These intermediates are also disclosed in J. Pharm. Sci. 57: 1364-69 (1968).

Mental illness encompasses both psychoses and neuroses. Symptoms requiring treatment include depression, anxiety, agitation, and hallucinations. Among the drugs used particularly for treatment of both reactive and endogenous depressions are monoamine oxidase (MAO) inhibitors, such as iproniazide, tranylcypromine, nialamide, phenelzine, and pargyline, and the non-MAO-inhibiting tricyclic aromatic dibenzazepines, such as imipramine, and dibenzocycloheptenes such as amitriptyline.

All of these drugs have adverse side effects that limit their usefulness. MAO inhibitors may benefit milder forms of depression, but the risk of serious toxic effects is a strong argument against their use. They can cause liver damage and acute hypertension, especially if given in conjunction with cheese, bananas, or other amine-containing foods. The MAO inhibitors can also cause tremors, insomnia, hyperhydrosis, agitation, hypermanic behavior, confusion, hallucinations, convulsions and orthostatic hypotension. They frequently cause dizziness, vertigo, headache, inhibition of ejaculation, difficulty in urination, weakness, fatique, dry mouth, constipation and blurred vision.

Imipramine can cause blurred vision, dryness of mouth, constipation, urinary retention, orthostatic hypotension, respiration depression, myocardial infarction, and congestive heart failure. Similar difficulties are experienced with amitriptyline.

There is a continuing need for psychotherapeutic agents that have fewer side effects than the drugs in use today; also for psychotherapeutic agents that have different modes of action than presently used agents, since none of these is completely effective.

The present invention results from efforts to develop new, safe, and effective psychotherapeutic compounds with minimal side effects.

SUMMARY OF THE INVENTION

According to this invention, there is provided novel compounds of formula I and their pharmaceutically suitable salts, compositions containing them, and methods of using them to alleviate depression in mammals.

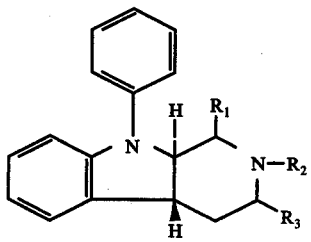

formula I wherein
$R_1$ = H, $CH_3$, or $C_2H_5$;

$R_2$ = H, $C_1$-$C_3$ alkyl or allyl;

$R_3$ = H, $CH_3$, or $C_2H_5$;

provided that the total number of carbon atoms in $R_1$ + $R_2$ + $R_3$ is not less than one and not more than four, and provided further that one of $R_1$ or $R_3$ must be other than H.

The compounds of formula I wherein $R_2$ = H and either $R_1$ or $R_3$ = $CH_3$ while the other = H are also useful as intermediates in the preparation of the other compounds of formula I.

DETAILED DESCRIPTION OF THE INVENTION

Preferred Embodiment

A compound of formula I most preferred because of its high degree of activity is the compound wherein $R_1$ is $CH_3$, $R_2$ is $C_2H_5$ and $R_3$ is H.

Pharmaceutical Salts

Pharmaceutically suitable acid addition salts of these compounds include those made with physiologically acceptable acids that are known in the art; such salts include hydrochloride, sulfate, phosphate, nitrate, citrate, maleate, and the like.

Stereoisomers

All compounds of formula I have at least two asymmetric centers, resulting from the reduction of the $\Delta^{4a,9a}$ to the trans-fused system. This invention includes the optically active enantiomers, as well as the racemic mixtures. In addition, any substituents at the 1 and/or the 3 position can exist as either cis or trans to the 4a H giving rise to further stereoisomeric forms; all the resulting diastereoisomers are also included in this invention.

Synthesis

The compounds of formula I can be obtained by methods outlined below in reaction schemes 1 and 2. The temperature listed in the following tables and examples are in degrees centigrade.

Reaction Scheme 1
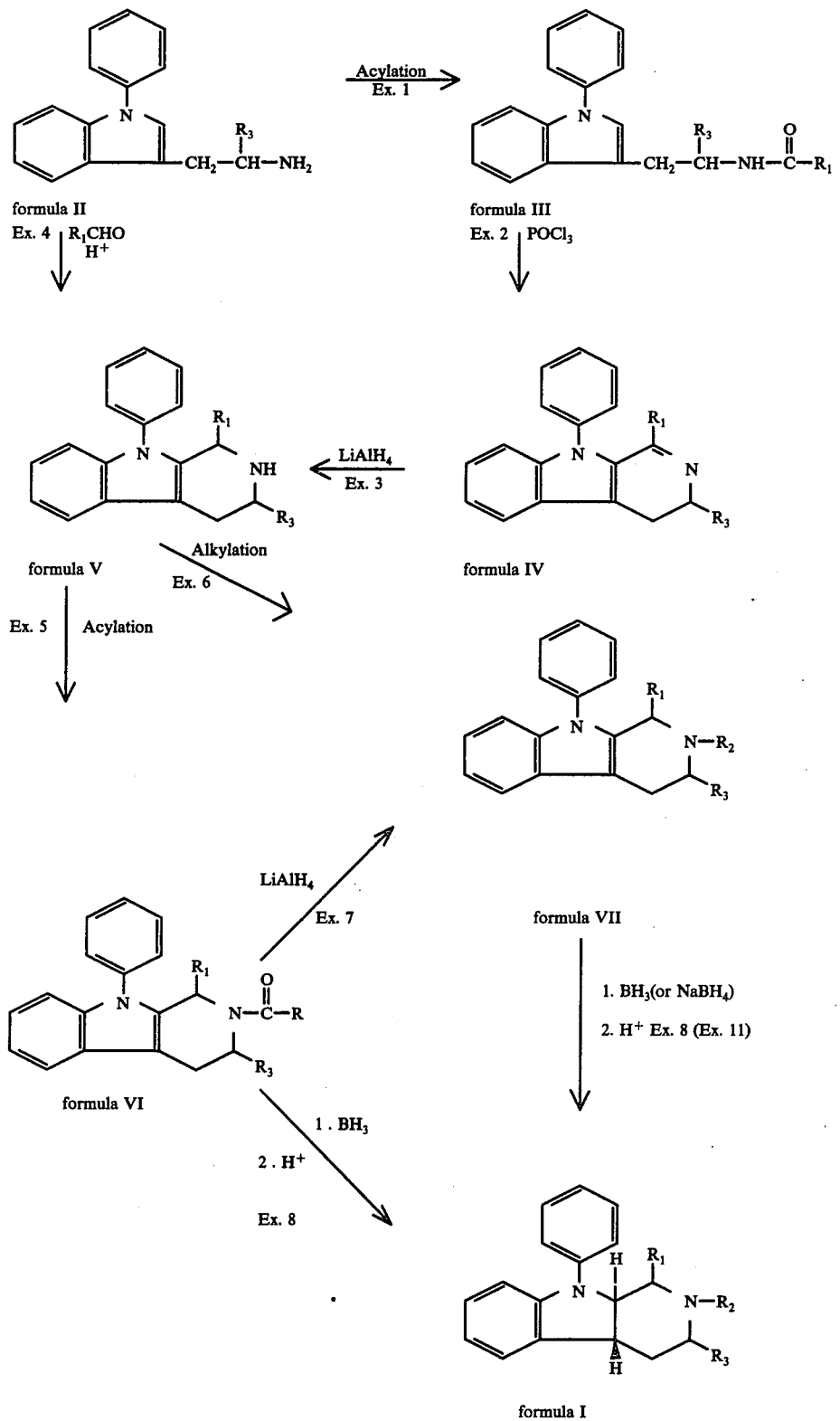
formula II
formula III
formula IV
formula V
formula VI
formula VII
formula I Reaction Scheme 2
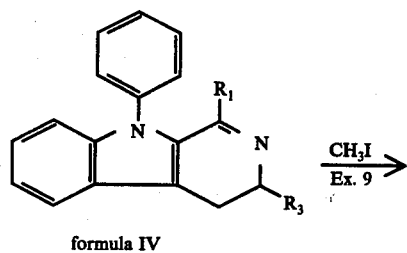
formula IV
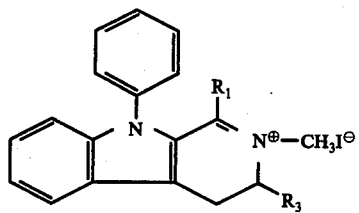
formula VIII
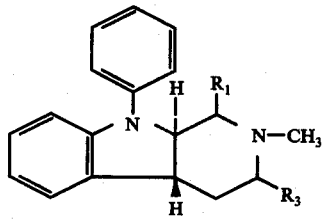
formula I (R$_2$=CH$_3$)
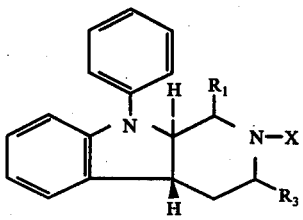
formula IXA (X = C-OC$_2$H$_5$)
formula IXB (X = C≡N)
Acylation
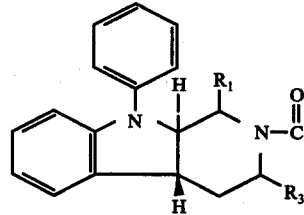
formula X

4,091,102

Reaction Scheme 3

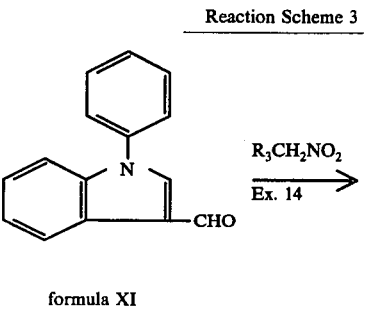

formula XI $R_3CH_2NO_2$ Ex. 14 →

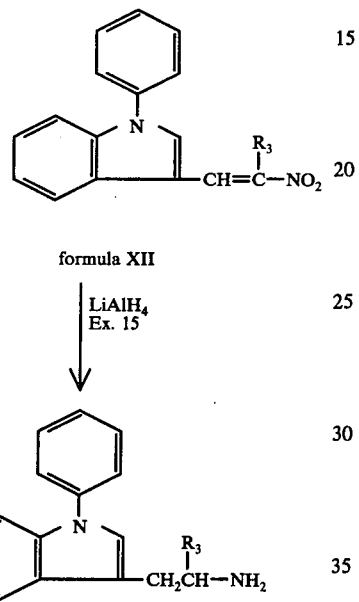

formula XII

↓ LiAlH$_4$ Ex. 15 formula II formula I

| | R$_1$ | R$_2$ | R$_3$ | m.p. (Salt) |
|---|---|---|---|---|
| Ia. | CH$_3$ | C$_2$H$_5$ | H | 131–133° |
| b. | CH$_3$ | CH$_3$ | H | 122–125° |
| c. | CH$_3$ | n-C$_3$H$_7$ | H | 244–246° (. HCl) |
| d. | CH$_3$ | i-C$_3$H$_7$ | H | 290° (. HCl) |
| e. | C$_2$H$_5$ | CH$_3$ | H | 134–136° |
| f. | C$_2$H$_5$ | C$_2$H$_5$ | H | 120–123° |
| g. | CH$_3$ | H | H | 95–97.5° |
| h. | CH$_3$ | CH$_2$CH=CH$_2$ | H | 104.5–105.5° |
| i. | H | CH$_2$CH=CH$_2$ | CH$_3$ | |
| j. | H | C$_2$H$_5$ | CH$_3$ | 192–195° (. HCl) |
| k. | CH$_3$ | C$_2$H$_5$ | CH$_3$ | |
| l. | C$_2$H$_5$ | H | H | |
| m. | H | CH$_3$ | C$_2$H$_5$ | |
| n. | CH$_3$ | CH$_3$ | C$_2$H$_5$ | |
| o. | CH$_3$ | H | CH$_3$ | |
| p. | C$_2$H$_5$ | H | CH$_3$ | |
| q. | CH$_3$ | H | C$_2$H$_5$ | |
| r. | H | i-C$_3$H$_7$ | CH$_3$ | |
| s. | CH$_3$ | CH$_3$ | CH$_3$ | |
| t. | C$_2$H$_5$ | CH$_3$ | CH$_3$ | |
| u. | H | H | CH$_3$ | | formula II

| | R$_3$ | m.p. (Salt) |
|---|---|---|
| IIa. | H | 232–233° (. HCl) |
| IIb. | CH$_3$ | 210–212° C. (. HCl) |
| IIc. | C$_2$H$_5$ | | formula III

| | R$_1$ | R$_3$ | m.p. |
|---|---|---|---|
| IIIa. | CH$_3$ | H | 122–125° C. |
| b. | C$_2$H$_5$ | H | 110–112° C. |
| c. | CH$_3$ | CH$_3$ | |
| d. | CH$_3$ | C$_2$H$_5$ | |
| e. | C$_2$H$_5$ | CH$_3$ | |
| f. | C$_2$H$_5$ | C$_2$H$_5$ | | formula IV

| | R$_1$ | R$_3$ | m.p. |
|---|---|---|---|
| IVa. | CH$_3$ | H | 110–112° C. |
| b. | C$_2$H$_5$ | H | 139–144° |
| c. | CH$_3$ | CH$_3$ | |
| d. | C$_2$H$_5$ | CH$_3$ | |
| e. | CH$_3$ | C$_2$H$_5$ | |
| f. | C$_2$H$_5$ | C$_2$H$_5$ | | formula V

| | R$_1$ | R$_3$ | m.p. |
|---|---|---|---|
| Va. | CH$_3$ | H | 85–87° |
| b. | C$_2$H$_5$ | H | 118–120° |
| c. | CH$_3$ | CH$_3$ | 185–190° (dec.) (. HCl) |
| d. | H | CH$_3$ | 200–208° (dec.) |
| e. | H | C$_2$H$_5$ | |
| f. | C$_2$H$_5$ | CH$_3$ | |
| g. | CH$_3$ | C$_2$H$_5$ | |

-continued

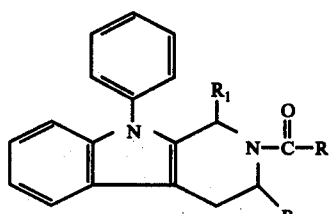

formula VI

| | R | $R_1$ | $R_3$ | m.p. |
|---|---|---|---|---|
| VIa. | $CH_3$ | $CH_3$ | H | 136–142° C. |
| b. | $CH_3$ | $C_2H_5$ | H | 114–117° C. |
| c. | $C_2H_5$ | $CH_3$ | H | 117–120° C. |
| d. | $CH_3$ | H | $CH_3$ | |
| e. | $CH_3$ | $CH_3$ | $CH_3$ | |
| f. | H | $CH_3$ | $C_2H_5$ | |
| g. | H | $CH_3$ | H | |
| h. | H | $CH_3$ | $CH_3$ | |
| i. | H | $C_2H_5$ | H | |

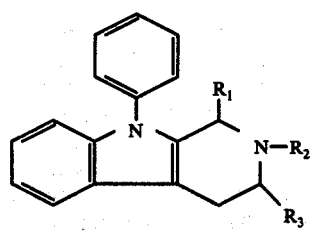

formula VII

| | $R_1$ | $R_2$ | $R_3$ | m.p. (Salt) |
|---|---|---|---|---|
| VIIa. | $CH_3$ | $CH_3$ | H | 235–240° (.HCl) |
| b. | $CH_3$ | $C_2H_5$ | H | 237–240° (.HCl) |
| c. | $C_2H_5$ | $CH_3$ | H | 245–251° (.HCl) |
| d. | $CH_3$ | $i\text{-}C_3H_7$ | H | 224–235° (.HCl) |
| e. | $C_2H_5$ | $CH_3$ | $CH_3$ | |
| f. | $CH_3$ | $CH_3$ | $C_2H_5$ | |
| g. | H | $C_2H_5$ | $C_2H_5$ | |
| h. | $CH_3$ | $n\text{-}C_3H_7$ | H | |
| i. | H | H | $CH_3$ | 200–208° (dec.) |
| j. | H | $C_2H_5$ | $CH_3$ | |
| k. | H | $i\text{-}C_3H_7$ | $CH_3$ | |
| l. | $CH_3$ | $CH_3$ | $CH_3$ | |

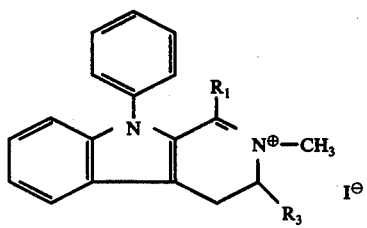

formula VIII

| | $R_1$ | $R_3$ | m.p. |
|---|---|---|---|
| VIIIa. | $CH_3$ | H | 221–223° C. |
| b. | $C_2H_5$ | H | 209–211° C. |
| c. | $C_2H_5$ | $CH_3$ | |
| d. | $CH_3$ | $C_2H_5$ | |
| e. | $CH_3$ | $CH_3$ | |

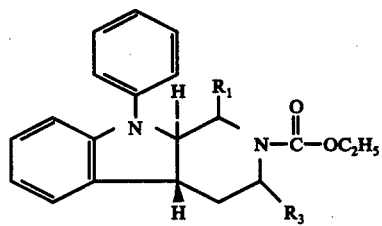

formula IXA

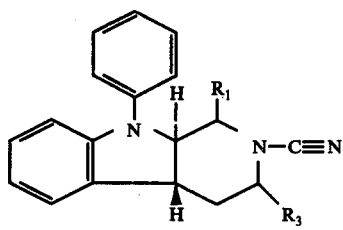

formula IXB

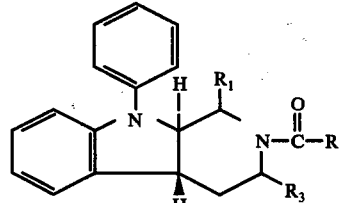

formula X

| | R | $R_1$ | $R_3$ | m.p. |
|---|---|---|---|---|
| Xa. | $CH_3$ | $CH_3$ | H | 136–142° |
| b. | $CH_3$ | H | $CH_3$ | 81–86° |
| c. | $C_2H_5$ | $CH_3$ | H | |
| d. | $CH_3$ | $C_2H_5$ | H | |
| e. | $CH_3$ | $CH_3$ | $CH_3$ | |
| f. | H | $CH_3$ | H | |
| g. | H | $CH_3$ | $CH_3$ | |
| h. | H | $C_2H_5$ | H | |

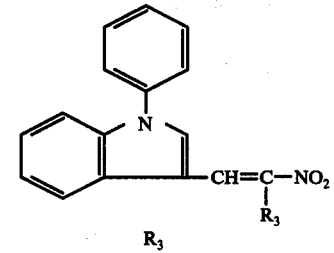

formula XII

| | $R_3$ | m.p. |
|---|---|---|
| XIIa. | H | 153–155°C. |
| b. | $CH_3$ | 104–105°C. |
| c. | $C_2H_5$ | |

A general procedure for preparation of compounds of formula I is as follows: Compounds of formula II are acylated with an anhydride, mixed anhydride, or an appropriate acyl halide in a basic solvent system to give the amides of formula III. These are converted to dihydropyridoindoles (formula IV) by the Bischler-Napieralski reaction using reagents such as phosphorous oxychloride, phosphorous pentoxide or polyphosphoric acid in a suitable solvent, such as benzene, xylene, toluene, or chloroform followed by reduction with lithium aluminum hydride or sodium bis(2-methoxyethoxy) aluminum hydride (Red-al®) to the tetrahydro pyridoindoles of formula V. These may also be obtained directly from formula II by the Pictet-Spengler reaction using an aldehyde of the type $R_1CHO$ in an acidic medium.

Acylation of formula V with an anhydride or an acid chloride or alkylation with a suitable alkyl halide or alkyl sulfate or sulfonate gives the compounds of formulas VI and VII respectively. Subsequent reaction of these with $BH_3$ or $NaBH_4$, followed by treatment with acid of the amine borane intermediates gives the hexahydropyridoindoles of Formula I.

Alternatively, compounds of formula IV can be quaternized with methyl iodide to formula VIII, then reduced with lithium aluminum hydride to formula VII, wherein $R_2 = CH_3$. Treatment with borane or $NaBH_4$ followed by acid gives the compounds of formula I wherein $R_2 = CH_3$. To convert the latter to compounds of formula I wherein $R_2$ is not H, two routes can be used. Reaction of the compound with

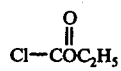

in benzene gives carbamates of formula IXA, which, upon hydrolysis with KOH in n-butanol gives the compounds of formula I wherein $R_2 = H$. In the preferred route, compounds of formula I wherein $R_2 = CH_3$ are treated with cyanogen bromide in chloroform to give the N-cyano compounds of formula IXB, which, without further purification, are converted to compounds of formula I wherein $R_2 = H$ by means of hydrolysis with dilute hydrochloric acid. Alkylation, or acylation and subsequent reduction of the amides (formula X) yields compounds of formula I wherein $R_2$ is not H.

Compounds of formula II can be prepared by the methods outlined in reaction scheme 3. Treatment of 1-phenylindole-3-carboxaldehyde (formula XI) with nitroalkanes gives the nitrovinyl indoles of formula XII. The amines of formula II can be obtained by the reduction of compounds of formula XII.

The following Examples further illustrate the preparation of these compounds.

EXAMPLE 1

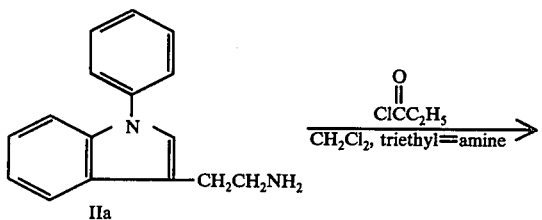

To a stirred solution of 30.2 g. of N-phenyltryptamine (IIa) in 500 ml. methylene chloride is added 21.0 g. triethylamine, followed by dropwise addition of a solution of 15.6 g. propionyl chloride in 75 ml. methylene chloride. The reaction mixture is stirred at room temperature overnight, poured into 600 ml. water, with stirring, the organic layer separated, dried over $Na_2SO_4$ and the solvent evaporated in vacuo. The dark orange oily residue is treated with a small amount of ether and petroleum ether (30°), the precipitated product chilled in an ice bath, filtered and 33.4 g. of light orange solids collected. Recrystallization from ethyl acetate-ether gives 30 g. of IIIb, m.p. 110°–112° C.

Compounds of formula IIIa–f exemplify those that can be prepared by the general acylation procedure described in Example 1.

EXAMPLE 2

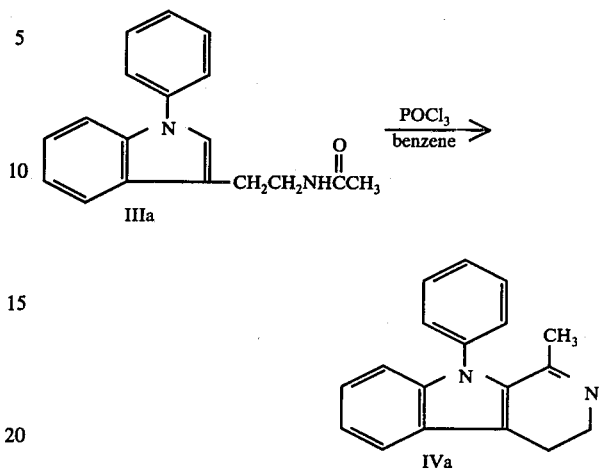

A mixture of 40.8 g. N-acetyl-1-phenyltryptamine (IIIa), 800 ml. dry benzene and 220 g. phosphorus oxychloride is refluxed for 1 hour. After cooling, the reaction mixture is poured into two liters of cold water with continued stirring and cooling for 1.5 hours. The organic layer is separated, washed twice with water and the aqueous fractions combined and backwashed once with ethyl acetate. The aqueous extract (total volume 3 liters) is treated with one liter of 10% NaOH, followed by one liter of 50% NaOH while stirring and cooling in an ice bath. The product precipitates from the cooled solution and is filtered and washed well with water to remove any co-precipitated inorganic material. Upon drying, 34 g. of 4,9-dihydro-1-methyl-9-phenyl-3H-pyrido[3,4-b]indole, (IVa), m.p. 110°–112° C. is obtained. An analytical sample had a m.p. 110°–112° C. (benzene-petroleum ether).

Anal. Calc'd for $C_{18}H_{16}N_2$ Calc'd: C: 83.04; H: 6.19; N: 10.76 Found: C: 83.21; H: 6.12; N: 10.74.

Compounds of formula IVa–f exemplify those that can be prepared by the Bischler-Napieralski reaction described in Example 2.

EXAMPLE 3

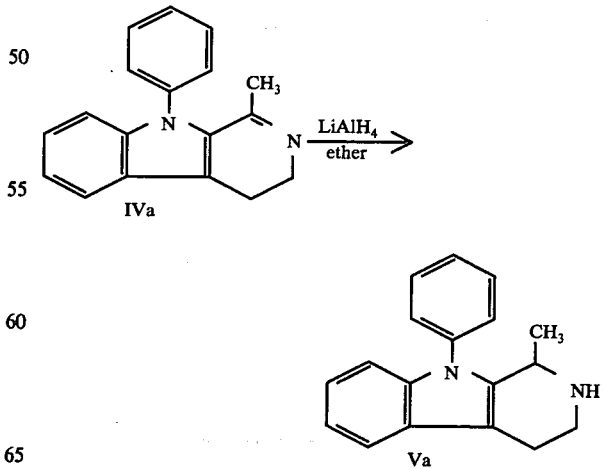

In a $N_2$ atmosphere, a solution of 18.8 g. of IVa in 550 ml. anhydrous ether is added dropwise to a stirred suspension of 11.1 g. LiAlH₄ in 500 ml. anhydrous ether over a one-hour period. The reaction mixture is refluxed for 5 hours, cooled in an ice bath and the excess LiAlH₄ is decomposed by the dropwise addition of 105 ml. water. The ether solution is decanted, dried over Na₂SO₄ and evaporated in vacuo to give a yellow solid. Crystallization from ether-petroleum ether gives 17.2 g. of V*a*. An analytical sample had a m.p. 85°–87° C.

Anal. Calc'd for $C_{18}H_{18}N_2$. Calc'd: C: 82.40; H: 6.92; N: 10.68; Found: C: 82.34; H: 6.84; N: 10.71.

EXAMPLE 4

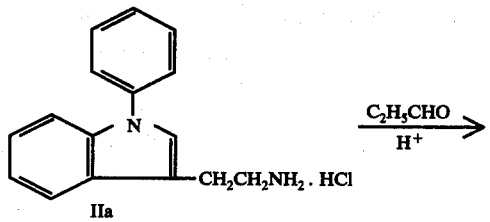

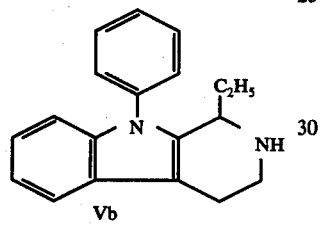

To a suspension of 5.2 g. of N-phenyltryptamine hydrochloride (II*a*) in 150 ml. water is added a total of 14.1 g. propionaldehyde (in 3 portions), 5 ml. ethanol and 21 ml. concentrated HCl (in 2 portions) while reaction mixture refluxes a total of 1 hour. After cooling, the mixture is washed with ether, the ether layer separated and backwashed with dilute HCl and the aqueous fractions combined. Upon shaking the aqueous fraction with fresh ether, the product precipitates as light gray solids that are filtered and collected to give 5.1 g. of V*b* hydrochloride. An analytical sample recrystallized from methanol-acetone had a m.p. 185°–190° C. (dec.).

Anal. Calc'd for $C_{19}H_{21}N_2Cl$. Calc'd: C: 72.95; H: 6.77; N: 8.95; Cl: 11.33. Found: C: 72.82; H: 6.73; N: 8.74; Cl: 11.38.

Compounds of formula V*a*–*g* exemplify those that can be prepared by the methods described in Examples 3 and 4.

EXAMPLE 5

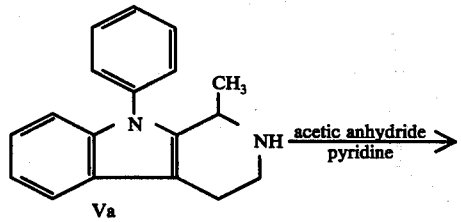

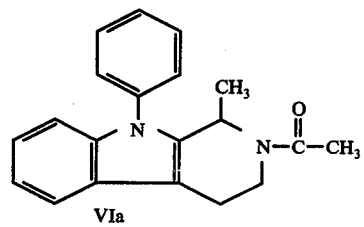

A mixture of 13.6 g. of V*a* in 50 ml. dry pyridine and 40 ml. acetic anhydride is allowed to stand at least 16 hours at room temperature, then poured into one liter of cold water with stirring. The mixture is extracted into ether and the ether extract washed with saturated NaCl solution, dried over Na₂SO₄ and evaporated in vacuo to a clear yellow oil. The product is crystallized from ether-petroleum ether to give 13.6 g. of VI*a* as granular cream white solids, m.p. 136°–142° C.

Compounds of formula VI*a*–*i* exemplify those that can be prepared by the general method of acylation of compounds of formula V as described in Example 5.

In a similar manner, but using compounds of formula I wherein R₂=H as starting materials, compounds of formula X*a*–*h* can be obtained.

EXAMPLE 6

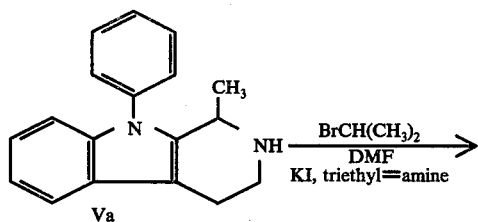

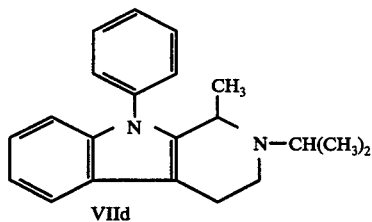

A mixture of 5.2 g. of V*a*, 12 g. of triethylamine, 8.4 g. of KI and 6.2 g. of 2-bromopropane in 50 ml. of dimethyl formamide is stirred at 50°–55° C. for 65 hours. After cooling, reaction mixture is poured into 800 ml. cold water, extracted into ether and the ether extract washed with saturated NaCl solution, dried over Na₂SO₄ and concentrated in vacuo to a dark oil. Treatment with ethereal HCl and crystallization from methanol-acetone gives 6.5 g. of VII*d* hydrochloride, m.p. 224°–235° C.

Compounds VII*d* and VII*h* exemplify those that can be obtained by the method described in Example 6. By utilizing compound I*g* as the starting material, compounds I*d*, and I*h* can be prepared by this same method, using the appropriate organic halide. When compound I*o* is the starting material, compound I*k* can be obtained in the same manner. Similarly, compounds I*i*, *j*, and *r* can be obtained from compound I*u*.

EXAMPLE 7

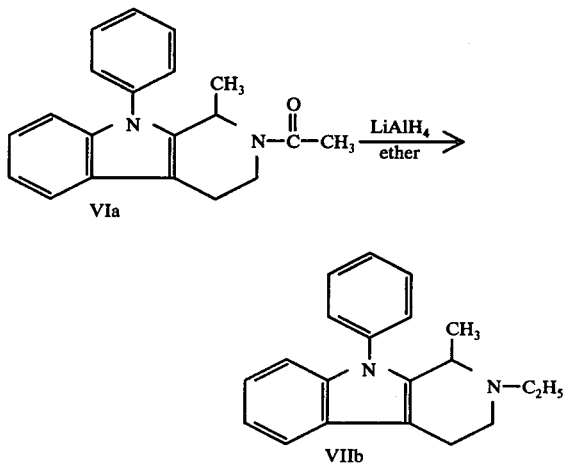

In a N₂ atmosphere, a solution of 1.9 g. of VI*a* in 100 ml. anhydrous ether is added dropwise to a stirred suspension of 850 mg. of LiAlH₄. The reaction mixture is refluxed for 2.5 hours, cooled in an ice bath and the excess LiAlH₄ destroyed by the dropwise addition of 10 ml. water. The ether solution is filtered, dried over Na₂SO₄ and concentrated in vacuo to a pale yellow oil. Treatment with ethereal HCl and crystallization from acetone gives 1.7 g. of VII*b* hydrochloride, m.p. 233°–236° C. An analytical sample had a m.p. 237°–240° C..

Anal. Calc'd for $C_{20}H_{23}N_2Cl$. Calc'd: C: 73.49; H: 7.09; N: 8.57; Cl: 10.85; Found: C: 73.22; H: 7.40; N: 8.49; Cl: 10.79.

Compounds VII*a, b, c, e, f, g, h, j* and *l* exemplify those that can be prepared by the method described in Example 7. By utilization of the compounds of formula X*a–h* as starting materials, the corresponding compounds of formula I can be obtained in a similar manner.

EXAMPLE 8

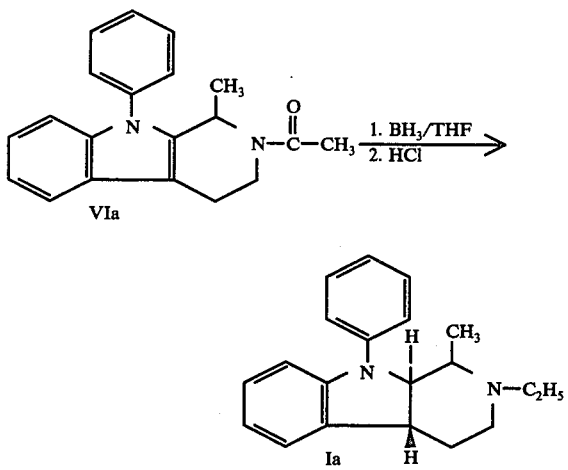

In a N₂ atmosphere, a solution of 33.0 g. of VI*a* in 800 ml. tetrahydrofuran is added dropwise to a stirred solution of 650 ml. 1 molar borane in tetrahydrofuran. The reaction mixture is refluxed for 18 hours and the solvent removed by distillation to give an almost colorless oily residue that solidifies upon cooling. Ten ml. of water is added dropwise, followed by 1200 ml. of 5N HCl, added slowly at first. After refluxing 3.5 hours, the reaction mixture is cooled and treated with 375 ml. of 50% NaOH without further cooling until the pH is >12. After cooling to room temperature, it is extracted into ether. The ether extract is washed with saturated NaCl solution, dried over Na₂SO₄ and the solvent removed in vacuo to give a pale yellow oil. Crystallization from ether-petroleum ether gives 17.3 g. of I*a*, m.p. 131°–133° C. An analytical sample had a m.p. 128°–129° C.

Anal. Calc'd for $C_{20}H_{24}N_2$. Calc'd C: 82.15; H: 8.27; N: 9.58; Found: C: 82.13; H: 8.25; N: 9.55.

Compounds I*a, c, f, j, k* exemplify those that can be prepared as illustrated in Example 8.

EXAMPLE 9

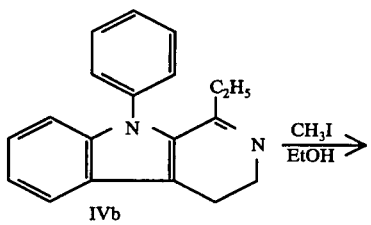

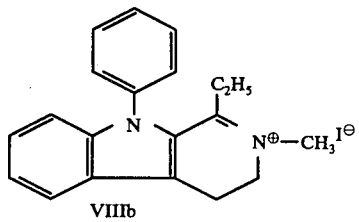

A mixture of 12.5 g. of IV*b* and 32 g. of iodomethane in 500 ml. of ethanol is refluxed for 4 hours. The product that precipitates upon concentration of the solution to ¼ volume in vacuo is filtered, washed with ethanol and ether, dried, and 14.9 g. of crude VIII*b* is collected. Crystallization from acetone and small amounts of methanol-ethyl acetate affords 9.3 g. of pure VIII*b*, m.p. 209°–211° C.

Compounds of formula VIII*a–e* exemplify those that can be prepared by the method illustrated in Example 9.

EXAMPLE 10

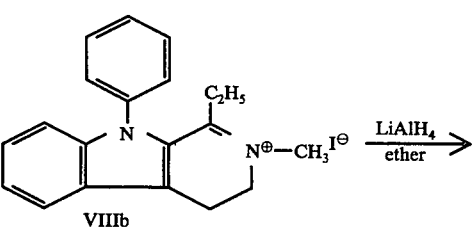

-continued

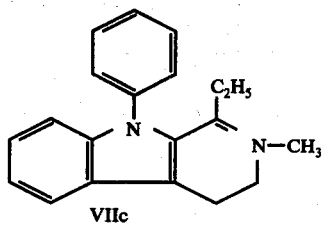

VIIc

To a stirred suspension of 3.5 g. of LiAlH₄ in 500 ml. of anhydrous ether in a N₂ atmosphere, is added 9.3 g. of VIIIb in small portions while maintaining the temperature of the reaction mixture between 17°–20° C. After the addition is complete, the reaction mixture is stirred at room temperature for one hour, cooled, and the excess LiAlH₄ decomposed by the dropwise addition of 35 ml. of water over a 45-minute period. The ether solution is filtered, dried and concentrated in vacuo to a cloudy oil. Treatment with ethereal HCl gives 7.3 g. of VIIc hydrochloride. After two recrystallizations from acetone-methanol, the analytical sample had a m.p. 245°–251° C. (dec.).

Anal. Calc'd for $C_{20}H_{23}N_2Cl$. Calc'd: C: 73.49; H: 7.09; N: 8.57; Cl: 10.85. Found: C: 73.30; H: 7.33; N: 8.58; Cl: 10.83.

Compounds VIIa, c, e, f and l exemplify those that can be prepared by the method described in Example 10.

EXAMPLE 11

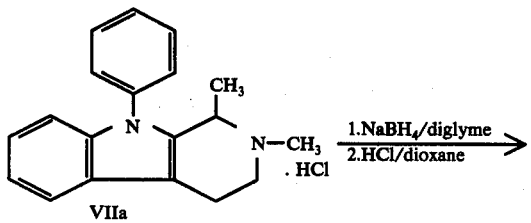

VIIa

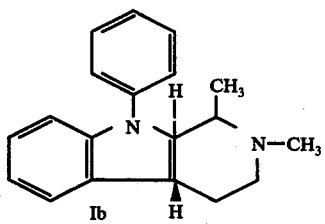

Ib

A solution of 4.4 g. of NaBH₄ in 50 ml diglyme (ethylene glycol dimethyl ether) is added dropwise to a stirred suspension of 32 g. of VIIa hydrochloride in 75 ml. diglyme in a N₂ atmosphere. After stirring one hour at room temperature, the reaction mixture is poured into 1 liter of water with stirring. The precipitated white solids are filtered and washed with water. The moist filter-cake is suspended in 150 ml. dioxane and 85 ml. of concentrated HCl is added. The mixture foams considerably and is slowly brought to reflux over a period of 1 hour. After refluxing 15 minutes, the solution is cooled in an ice bath and treated with 10% NaOH until pH > 10. Dilution with an equal volume of water to a total volume of 1400 ml. and cooling in an ice bath precipitates the product as white solids which are filtered, washed with water and collected to give 27.2 g.

of Ib. An analytical sample recrystallized from acetone-methanol had a m.p. 122°–125° C.

Anal. Calc'd for $C_{19}H_{22}N_2$. Calc'd: C: 81.97; H: 7.96; N: 10.06; Found: C: 81.91; H: 7.96; N: 10.08.

Compounds of formula Ia, b, c, d, e, f, j, k, m, n, r, s and t can be prepared by the method described in Example 11, however they can also be prepared using the BH₃ method illustrated by Example 8.

EXAMPLE 12

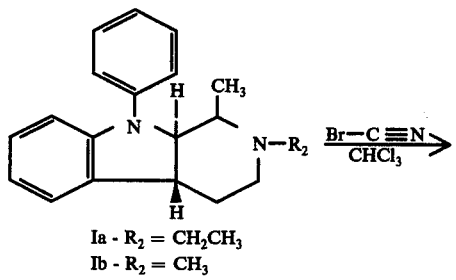

Ia - R₂ = CH₂CH₃
Ib - R₂ = CH₃

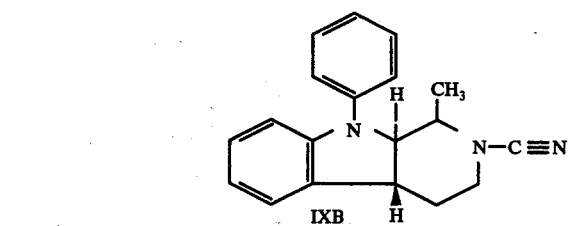

IXB

In a well ventilated hood, a solution of 8.0 g. of cyanogen bromide in 35 ml. chloroform is added to a solution of 7.5 g. of Ia in 35 ml. chloroform. The resulting clear solution is heated to reflux for 6 hours. The reaction mixture is then evaporated to dryness to yield a blue oil which is washed with n-pentane. On digestion with ethanol, a solid, m.p. 145°–147°, is obtained.

Using the same procedure, but starting with Ib instead of with Ia, the identical material is obtained.

EXAMPLE 13

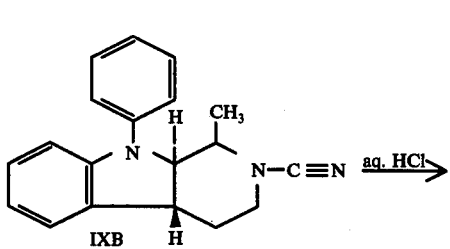

IXB

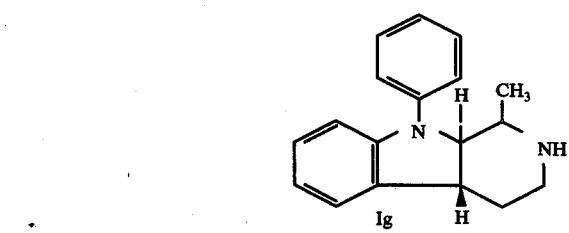

Ig

Without further purification, 5.0 g. of the cyanamide IXB from Example 12 is suspended in 60 ml. of 5N aqueous hydrogen chloride, and the resulting suspension is refluxed for six hours. On cooling, the lilac precipitate is filtered and triturated with ethyl acetate to give I*g* hydrochloride, m.p. 242°–246°.

A solution of I*g* hydrochloride is dissolved in water, the solution is basified with 50% NaOH, and I*g* as the free base is obtained, m.p. 95°–97.5°.

Anal. Calc'd for $C_{18}H_{20}N_2$. Calc'd: C: 81.78; H: 7.63; N: 10.60. Found: C: 81.84; H: 7.66; N: 10.52.

Compounds of formula I*g*, *l*, *o*, *p*, *q* and *u* exemplify those that can be prepared by the method described in Example 13.

EXAMPLE 14

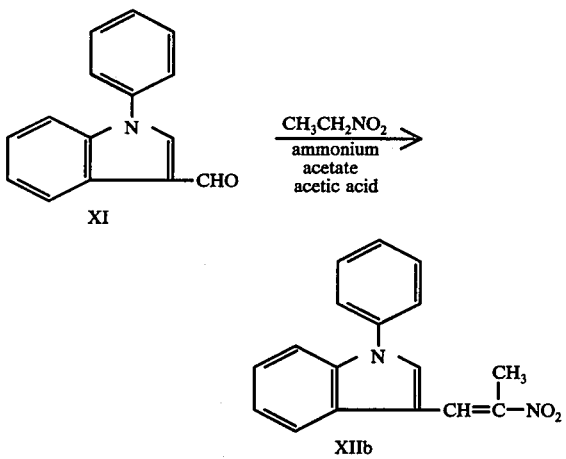

A mixture of 6.88 g. of phenylindole-3-carboxaldehyde XI, 11.6 g. of nitroethane and 0.7 g. of ammonium acetate in 25 ml. of glacial acetic acid is refluxed for 5 hours. Evaporation of the solvent in vacuo gives a dark yellow oil. Crystallization from ethanol-water and ethanol gives 2.8 g. of XII*b* as a yellow solid, m.p. 104°–105° C.

Compounds of formula XII*a–c* can be obtained by this method.

EXAMPLE 15

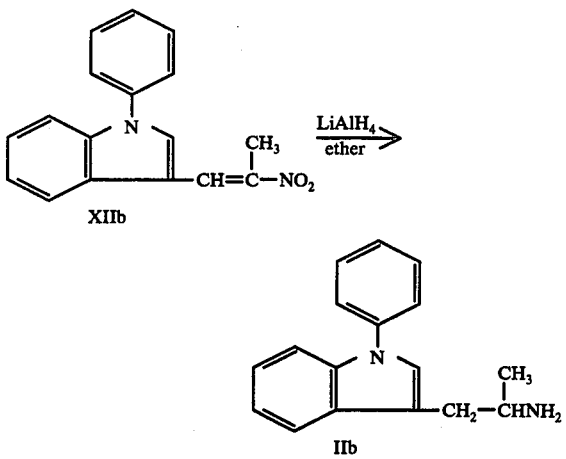

To a stirred suspension of 2.8 g. of LiAlH₄ in 100 ml. anhydrous ether in a N₂ atmosphere is added dropwise a solution of 2.8 g. of XII*b* in 100 ml. of anhydrous ether and 30 ml. of dry benzene. The reaction mixture is refluxed one hour, cooled, and the excess LiAlH₄ decomposed by the dropwise addition of 28 ml. of water. The ether solution is filtered, dried over $Na_2SO_4$ and concentrated in vacuo to a pale yellow oil. Treatment with ethereal HCl precipitates the product which is filtered and dried to give 2.5 g. of II*b* hydrochloride. Crystallization from ethanol gives 1.4 g., m.p. 210°–212° C.

Compounds of formula II*a–c* can be prepared as illustrated by the method described in Example 15.

Dosage Forms and Use

The antidepressant agents of this invention can be administered as treatment for psychiatric depressions of the reactive and endogenous types by any means that produces contact of the active agent with the agent's site of action in the body of a mammal. In addition to their antidepressant activity they also have a beneficial sedative action. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon know factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.2 to 100 milligrams per kilogram of body weight. Ordinarily 1 to 20, and preferably 2 to 10 milligrams per kilogram per day given in divided doses 2 to 4 times a day or in sustained release form is effective to obtain desired results.

Dosage forms (compositions) suitable for internal administration contain from about 50 milligrams to about 100 milligrams of active ingredient per unit. In these pharmaceutical compositions the active ingredient will ordinarily be present in an amount of about 0.01–90% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA (ethylenediaminetetraacetic acid). In addition parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

Capsules can be prepared by filling standard two-piece hard gelatin capsules with the following mixture using conventional encapsulating equipment:

| | |
|---|---|
| Active ingredient | 75 mg. |
| Lactose | 225 mg. |
| Talc | 25 mg. |
| Magnesium stearate | 8 mg. |

Capsules

A mixture of active drug in soy bean oil is prepared and injected by means of a positive displacement pump in gelatin to form soft gelatin capsules containing 75 mg. of the active ingredient. The capsules are washed in petroleum ether and dried.

Tablets

Tablets can be prepared by conventional procedures so that each unit will contain:

| | |
|---|---|
| Active ingredient | 75 mg. |
| Spray dried lactose | 100 mg. |
| Microcrystalline cellulose | 50 mg. |
| Magnesium stearate | 3 mg. |

Parenteral

Parenteral composition suitable for intra muscular administration is prepared so that each ml. contains:

| | |
|---|---|
| Active ingredient | 75 mg. |
| Sodium carboxy methyl cellulose | 75% |
| Polysorbate 80 | 0.04% |
| Benzyl alcohol | 0.9 % |
| Sodium chloride | 0.9 % |
| Water for injection Q.S. | 1 ml. |

Suspension

An aqueous suspension is prepared for oral administration so that each 5 mls. contain:

| | |
|---|---|
| Active ingredient | 75 mg. |
| Methylcellulose | 5 % |
| Carboxy methyl cellulose | 5 % |
| Syrup | 30 % |
| Polysorbate 80 | 0.2 % |
| Sodium saccharin | 2 mg. |
| Cherry flavor | 0.1 % |
| Sodium benzoate | 5 mg. |

| | |
|---|---|
| *-continued* | |
| Water Q.S. | 5 ml. |

A standard procedure for detecting and comparing the antidepressant activity of compounds in this series for which there is good correlation with human efficacy is the prevention of tetrabenazine-induced sedation and depression in mice. (Everett, "The Dopa Response Potentiation Test and Its Use in Screening for Antidepressant Drugs", pp. 164–167 in "Antidepressant Drugs" [Proceedings of the First International Symposium], S. Garattini and M. N. G. Dukes, eds., 1967.).

Groups of 10 Carworth $CF_1S$ female mice, 18–21 g. each, were fasted 1.5 hours and were intubated with antagonist compounds at oral doses of 0, 5, 25, and 125 mg/kg or 0, 1, 3, 9, 27, and 81 mg/kg in 0.20 ml. of 1% Methocel (methylcellulose). The mice were challenged 30 minutes later with tetrabenazine (as the methane-sulfonate), 32 mg/kg intraperitoneally (dissolved in 0.20 ml. 0.05M KCl at pH 2.0). One hour after antagonist (30 minutes after tetrabenazine), the mice were examined for signs of exploratory activity and ptosis (eyelid closure). Normal exploratory activity (relief from sedation) was recorded when a mouse lifted by the tail from a group of 10 in a testing box and placed on a stainless steel testing box lid (12.5 × 8 inches with 0.33 inch mesh) either turned its head horizontally 30° in both directions or moved to the edge of the screen within 10 seconds after being placed on the screen. Relief from ptosis was recorded when exactly 2 seconds after placing the mouse facing the observer, lid closure was less than 50% in both eyes. The following table gives results.

ANTAGONISM OF TETRABENAZINE-INDUCED DEPRESSION IN MICE ORALLY AT 1 HOUR POST-DRUG

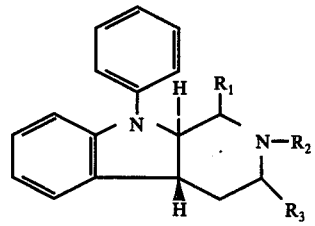

| COMPOUND | | | $ED_{50}$ (mg/kg) FOR PREVENTION OF | |
|---|---|---|---|---|
| $R_1$ | $R_2$ | $R_3$ | EXPLORATORY LOSS | PTOSIS |
| $CH_3$ | $C_2H_5$ | H | 4.2 | 3.0 |
| $CH_3$ | $CH_3$ | H | 38 | 16 |
| $CH_3$ | $n-C_3H_7$ | H | 38 | 14 |
| $CH_3$ | $i-C_3H_7$ | H | 19 | 11.2 |
| $C_2H_5$ | $CH_3$ | H | 11.2 | 9.1 |
| $C_2H_5$ | $C_2H_5$ | H | 38 | 27 |
| $CH_3$ | H | H | 31 | 25 |
| H | $C_2H_5$ | $CH_3$ | <5 | <5 |
| Amitriptyline | | | 4.7 | 1.7 |

I claim:

1. A compound of the formula

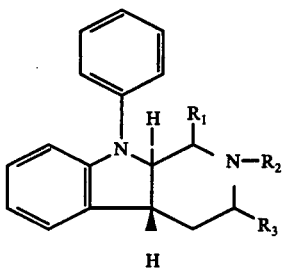

wherein $R_1$ = H, $CH_3$, or $C_2H_5$;

$R_2$ = H, $C_1$-$C_3$ alkyl or allyl;

$R_3$ = H, $CH_3$, or $C_2H_5$;

provided that the total number of carbon atoms in $R_1 + R_2 + R_3$ is not less than one and not more than four, and provided further that one of $R_1$ or $R_3$ must be other than H; and its pharmaceutically suitable salts.

2. The compound of claim 1: (±)-trans-2-ethyl-2,3,4,4a,9,9a-hexahydro-1-methyl-9-phenyl-1H-pyrido[3,4-b]indole.

3. The compound of claim 1: (±)-trans-2-ethyl-2,3,4,4a,9,9a-hexahydro-3-methyl-9-phenyl-1H-pyrido[3,4-b]indole.

4. A pharmaceutical composition comprising a suitable pharmaceutical carrier and an effective antidepressant amount of a compound of claim 1.

5. A pharmaceutical composition comprising a suitable pharmaceutical carrier and an effective antidepressant amount of a compound of claim 2.

6. A pharmaceutical composition comprising a suitable pharmaceutical carrier and an effective antidepressant amount of a compound of claim 3.

7. A method of alleviating depression in a mammal which comprises administering to the mammal an effective antidepressant amount of a compound of claim 1.

8. A method of alleviating depression in a mammal which comprises administering to the mammal an effective antidepressant amount of a compound of claim 2.

9. A method of alleviating depression in a mammal which comprises administering to the mammal an effective antidepressant amount of a compound of claim 3.

* * * * *